United States Patent [19]

Valtchev

[11] 4,022,208
[45] May 10, 1977

[54] GYNECOLOGIC INSTRUMENT

[76] Inventor: Konstantin L. Valtchev, 15 La Rose Ave., Apt. No. 1614, Weston, Ontario, Canada, M9P 1A7

[22] Filed: Nov. 7, 1975

[21] Appl. No.: 629,792

Related U.S. Application Data

[63] Continuation-in-part of Ser. No. 491,826, July 25, 1974, abandoned.

[52] U.S. Cl. .............................. 128/239; 128/303 R
[51] Int. Cl.² .................. A61B 17/42; A61M 31/00
[58] Field of Search ......................... 128/303 R, 239

[56] References Cited

UNITED STATES PATENTS

| 1,559,737 | 11/1925 | Bock | 128/345 |
| 2,482,622 | 9/1949 | Kahn | 128/321 X |
| 3,796,211 | 3/1974 | Kohl | 128/2 B |
| 3,809,091 | 5/1974 | Shute | 128/303 R |
| 3,877,433 | 4/1975 | Librach | 128/303 R |

*Primary Examiner*—Channing L. Pace

[57] ABSTRACT

This invention relates to a gynecologic instrument comprising a stem, a uterine hook, said uterine hook being pivotally mounted adjacent one of its ends to an end of said stem for angular adjustment with respect to the stem, and control means connecting with said uterine hook and extending therefrom to a location adjacent the end of said stem that is remote from the end where said uterine hook is connected for controllably turning said hook about its connection with said stem. There is also disclosed a method of using this instrument.

11 Claims, 5 Drawing Figures

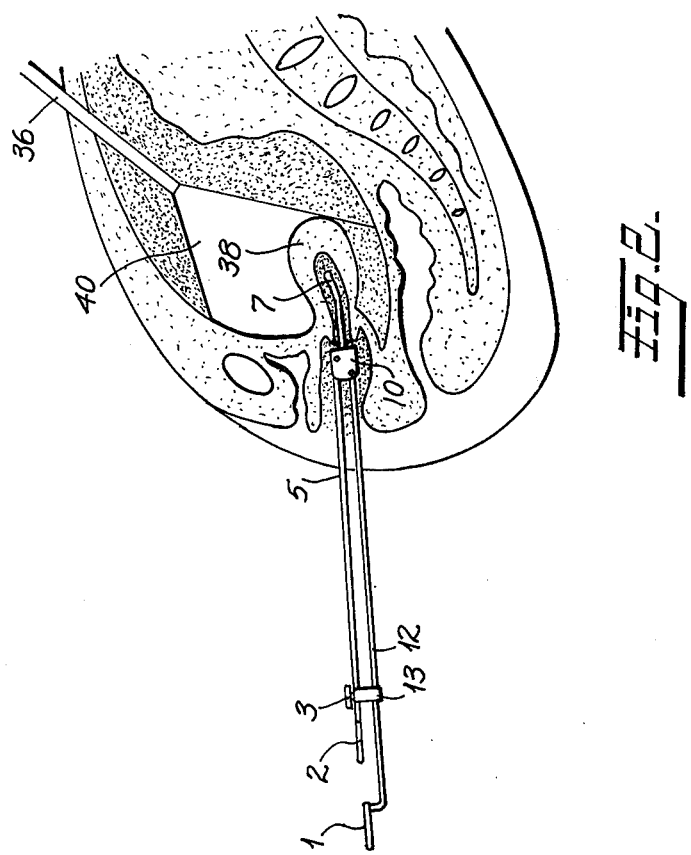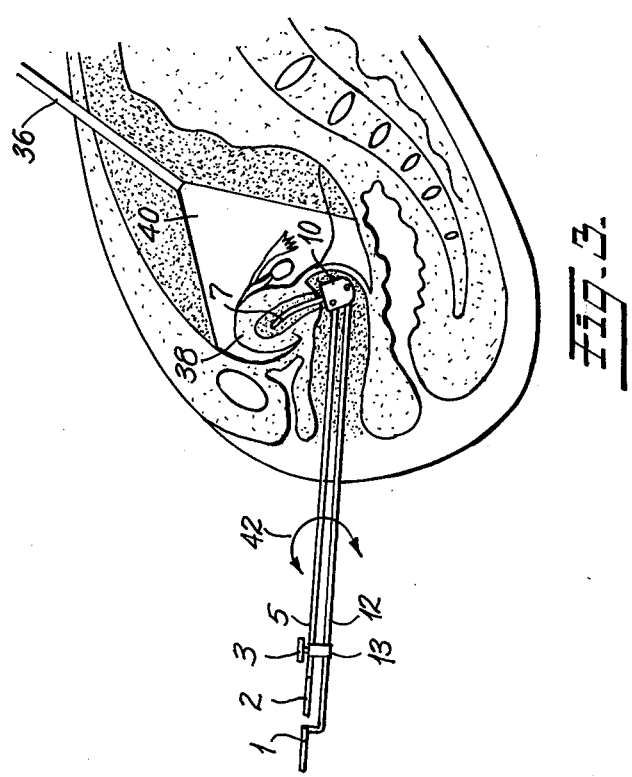

GYNECOLOGIC INSTRUMENT

This application is a continuation-in-part of U.S. Pat. Application 491,826 filed July 25, 1974 now abandoned.

This invention relates to a gynecologic instrument useful in gynecologic laparoscopy.

Gynecologists commonly examine the internal pelvic organs by means of a laparoscope and the procedure of using a hook to control the position of the uterus and its appendages for the purpose of obtaining a better view is well established. The commonly used uterine hook enters the uterus and has a shank that extends therefrom and through the vaginal opening. The position of the uterus is controlled by manoeuvring the stem of the instrument in the vaginal opening.

The general procedure is a valuable one but its scope is limited by the limitations of the rigid uterine cannula used for moving the uterus to various positions in the peritoneal cavity. Only a relatively limited movement can be achieved because the rigid cannula cannot rotate the uterus to all of its natural positions because of the danger of damaging vaginal tissue with the shank of the cannula.

One of the techniques that may be used by gynecologists conducting such diagnostic procedures is the injection of dye within the uterus. The gynecologist may then observe the flow of dye either using a laparoscope or X-ray techniques to determine various conditions. Present equipment used for inserting such dyes is inadequate in that dye cannot be inserted at a time when the uterus has been rotated to a position close to the abdominal wall.

It is an object of this invention to provide a gynecologic instrument capable of rotating the uterus to any of its natural positions within the peritoneal cavity which instrument lessens the danger of damage to vaginal and uterine tissue and which instrument may be adopted for injection of dye into a uterus while the uterus is maintained in any of its natural positions.

A gynecologic instrument according to the present invention comprises a stem, a uterine hook mounted in a block, said block being pivotally affixed to the proximal end of said stem for angular adjustment of said block and said hook with respect to the stem, and control means connecting the proximal end thereof with said block and extending therefrom to a location adjacent the distal end of said stem that is remote from the distal end where said block is connected for controllably turning said block and said hook about said connection with said stem, said block having a cervix engaging shoulder to limit penetration of said hook into a uterus and a smooth part-spherical vaginal wall engaging surface for supporting said instrument.

The invention will be clearly understood after reference to the following detailed specification read in conjunction with the drawings.

In the drawings:

FIGS. 2 and 3 are schematic illustrations of its manner of use; and

Figure 1:
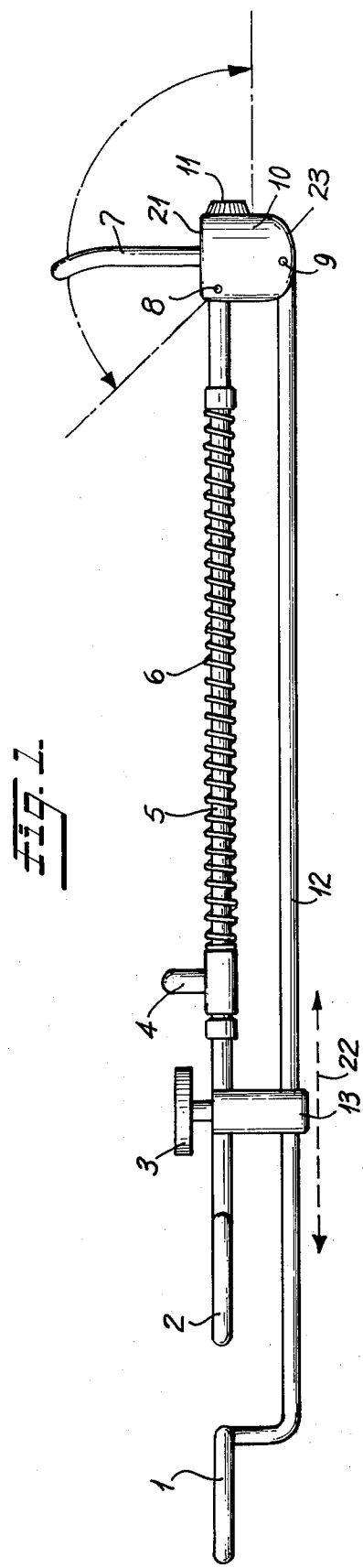
FIG. 1 is a side view of an instrument according to the invention.
Figure 4:
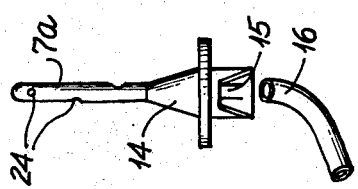

FIG. 4 which is on the sheet containing FIG. 1, illustrates a uterine hook suitable for fluid injection.

The instrument illustrated has a stem 12 and a block 10 pivotally mounted on the stem by pin 9. Block 10 has a substantially flat cervix engaging shoulder 21 that is adapted to abut the vaginal part of the uterus cervix in use as will be explained later.

Figure 1A:
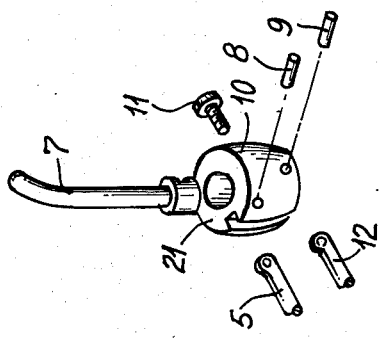
FIG. 1A is a partial exploded view of the block.

As can best be seen in FIG. 1A, hook 7 is inserted into a recess of block 10 and retained therein by means of set screw 11 that threads into block 10 to engage with the bore of the hook 7.

The control link 5 has an extension 13 at its free end. The extension 13 has a through bore so that it can slide freely along stem 12. A thumb screw 3 threadedly engages in extension 13 and can be turned to tighten against stem 12 to lock the link 5 with respect to stem 12 and fix the angular position of block 10 and hook 7 with respect to stem 12.

Thus, the hook 7 can be manipulated to any desired angular position with respect to the stem 12 and maintained in that position by the set screw 3.

A control link 5 pivotally connects the proximal end thereof with the block 10 by pin 8 and extends from its pivotal connection therewith to adjacent the free distal end of the stem 12. It is formed with a gripping ring 2. Stem 12 is also formed with a gripping ring 1 at the distal end thereof and, in use, a surgeon can, by moving the gripping rings 1 and 2 away from or towards each other in the directions of the arrows 22, rotate block 10 about its pivotal connection with stem 12. Thus, hook 7 can be caused to move from one dotted line position shown in FIG. 1, through the solid line position to the other dotted line position whereby to move the hook to any desired angular position with respect to the stem 12. While a greater arc of rotation may be provided the instrument will usefully serve its intended function if the block 10 is pivoted about pin 9 so as to permit movement of hook 7 through an arc of at least approximately 135°. To achieve full natural rotation of the uterus, link 5 must be capable of pivoting hook 7 from a position where stem 12 and hook 7 are substantially parallel to a position where the angle between stem 12 and hook 7 is not greater than 45°.

Block 10 includes a substantially part spherical surface 23 opposite shoulder 21. This surface must be smooth in order to minimize the chances of injury to sensitive vaginal tissue during rotation of block 10 about pin 9. A part spherical surface is the most desirable shape although other smooth contours may be employed. As the uterus is moved by the movement of hook 7, ligaments attached to the uterus may cause the instrument to be pressed against the vaginal wall. Thus, the smooth part spherical surface will distribute any such pressure and support the instrument and uterus throughout the full range of possible positions. Shoulder 21 ensures that excess penetration of hook 7 will not occur during movement of the uterus. A range of sizes of hook 7 may be provided to accommodate any particular patient or condition. A properly chosen hook size and the action of shoulder 21 will together eliminate the danger of perforating the uterus during use of the instrument. Block 10 also includes a slot or opening into which pass stem 12 and control link 5. This slot provides a simple method of ensuring that the full desired range of angular movement is possible without the need for any unnecessary projections from block 10 which might damage vaginal tissue.

FIGS. 2 and 3 are schematic illustrations of a gynecologic laparoscopy showing the patient in Trendelenburg position and the laparoscope 36 in position to view the uterus 38. The field of vision of the laparoscope is indicated by the numeral 40. The instrument may be used in association with a tenaculum in the conventional manner. Coil spring 6 wound on control link 5 and sliding fitting 4 facilitate such use.

The hook 7 of the instrument is inserted into the uterus through the vaginal opening until the cervix engaging shoulder 21 abuts against the cervix of the uterus. Shoulder 21 thus limits the depth of penetration of hook 7 into the uterus and also supports the uterus as it is moved to the desired position. By manipulation of the gripping rings 1 and 2 towards or away from each other a surgeon can support the uterus in any position in a vertical or medium sagittal plane from the one illustrated in FIG. 2 to the one illustrated in FIG. 3. This range of vertical positioning gives excellent opportunity for laparoscope inspection. As shown in FIG. 3 the uterus may be flexed to the natural position closest to the abdominal wall. By tightening set screw 3 one can fix the hook 7 in any desired angular position with respect to the stem 12. Thus, the uterus may be maintained at any desired position in the vertical or median sagittal plane. After the uterus has been located in a desired position, the instrument may be rotated about the longitudinal axis of stem 12 in the direction of the arrow 42 shown in FIG. 3. Thus, the uterus may be rotated either to the left or right while close to the abdominal wall giving the surgeon an excellent lateral view.

The instrument may be easily modified to facilitate injection of gases or liquid into the uterus by making the hook 7 tubular in nature and providing a gas or liquid conduit to the base of the hook as a gas or liquid supply line. As shown in FIG. 4, a tubular hook 7a may be provided with openings 24 for passage of fluid. In order to provide a useful fluid seal between hook 7 and the vaginal opening of the uterus, a cone-shaped shoulder 14 can advantageously be incorporated. However, shoulder 14 should not be so broad as to be co-extensive with shoulder 21 as this would then entail loss of the penetration limiting function of shoulder 21. The hook 7a may be provided with a tubular extension 15 by means of which a flexible conduit 16 may be fluidly connected to hook 7a. The conduit could most advantageously pass from the end of such a tubular portion 15 of hook 7a through the aforesaid slot in block 10 and thence in a direction parallel to stem 12. Fluid can then be passed through the tube by means of a syringe or other conventional means. As an alternative, block 10 might contain a passageway in fluid communication with the tubular portion of hook 7a. The supply line could then be connected to the passageway in said block. It is considered that passing the supply conduit through the slot in the block as described hereinbefore will eliminate any extra projections from the otherwise smooth surface of block 10 and will at the same time minimize any chance of the supply tube becoming blocked through crimping. Such a modified instrument provides the gynecologist with the ability to inject gases or liquids including dyes while the uterus is maintained in any of its natural positions.

The general method of performing a gynecologic laparoscopy is well known and not referred to in detail. It is well described in the book, "Laparoscopy, Culdoscopy and Gynecography," by Melvin R. Cohen, published 1970 by W. B. Saunders Company of Philadelphia, Pa. London, Ontario and Toronto, Ontario.

What I claim is:
1. A gynecologic instrument comprising:
 a. a stem having a proximal end and a distal end,
 b. a uterine hook,
 c. a block,
 d. said uterine hook being mounted in said block and said block being pivotally affixed to the distal end of said stem for angular adjustment of said block and said hook with respect to said stem,
 e. said block having a flat surface from which said hook projects and a smooth part-spherical surface at a portion of said block remote from said flat surface,
 f. and a control link having a proximal end and a distal end and being generally parallel to and spaced from said stem pivotally affixed at its distal end to said block and with its proximal end being adjacent the proximal end of said stem for controllably pivoting said block about its connection to said stem by reciprocal movement of said link relative to said stem,
 g. said hook and said block adapted to be movable through an arc from a first position where said uterine hook and said stem are substantially parallel to a second position substantially more than 90° remote from said first position.

2. A gynecologic instrument as claimed in claim 1, in which said control link pivotal connection with said block being in spaced relation to the connection of the block with the stem for pivotal movement about an axis parallel to the pivotal axis of the block with respect to the stem, the principal axis of said control link extending from its point of pivotal connection with said block to adjacent the distal end of said stem, and gripping means adjacent the distal ends of said stem and said link for manually manipulating the longitudinal axis of said link and the longitudinal axis of said stem relative to each other to turn said block about its mounting on said stem.

3. A gynecologic instrument as claimed in claim 2, having means for releasably maintaining the position of said link with respect to said stem.

4. The instrument of claim 2, wherein said uterine hook comprises a tubular portion having an opening for passage of fluid therethrough.

5. The instrument of claim 4, wherein said block comprises a passageway therethrough in fluid connected relationship with said tubular portion of said hook.

6. The instrument of claim 4, wherein a tubular conduit is connected to said tubular portion in fluid connected relationship whereby fluid may be passed through said tubular conduit and through said tubular portion.

7. The instrument of claim 5, wherein a tubular conduit is connected to said passageway in fluid connected relationship whereby fluid may be passed through said tubular conduit, said passageway and said tubular portion.

8. A method of pivoting the uterus in a human female to the natural position closest to the abdominal wall comprising inserting the uterine hook of the instrument claimed in claim 1, into the vaginal opening of the uterus until the said flat surface engages the cervix of the uterus while said instrument is in said first position, and thereafter reciprocating said control link relative to said stem to cause said uterine hook and said uterus to pivot to said second position.

9. A method of injection of fluid into the uterus of a human female when said uterus is in a desired position which position is a naturally occurring position of said uterus comprising inserting the tubular uterine hook of the instrument claimed in claim 4, into the vaginal opening of the uterus until the said flat surface engages the cervix of the uterus while said instrument is in said first position, and thereafter reciprocating said control link relative to said stem to cause said uterine hook and said uterus to pivot to said desired position and thereafter causing fluid to pass through said tubular conduit and said tubular portion of said hook.

10. A method of injection of fluid into the uterus of a human female when said uterus is in a desired position which position is a naturally occurring position of said uterus comprising inserting the tubular uterine hook of the instrument claimed in claim 5 into the vaginal opening of the uterus until the said flat surface engages the cervix of the uterus while said instrument is in said first position, and thereafter reciprocating said control link relative to said stem to cause said uterine hook and said uterus to pivot to said desired position and thereafter causing fluid to pass through said tubular conduit, said passageway and said uterine hook.

11. A method of locating the uterus in a human female in any desired natural position comprising the steps of inserting the uterine hook of the instrument claimed in claim 1 into the vaginal opening of the uterus until said flat surface engages the cervix of the uterus, reciprocating said control link relative to said stem to cause said stem and said uterus to pivot in the median sagittal plane to the desired angular inclination in said median plane and thereafter rotating said instrument about the longitudinal axis of said stem whereby said uterus is moved to said desired position.

* * * * *